United States Patent [19]
Pokora et al.

[11] Patent Number: 5,374,555
[45] Date of Patent: Dec. 20, 1994

[54] PROTEASE CATALYZED TREATMENTS OF LIGNOCELLULOSE MATERIALS

[75] Inventors: Alexander R. Pokora, Pickerington; Mark A. Johnson, Chillicothe, both of Ohio

[73] Assignee: The Mead Corporation, Dayton, Ohio

[21] Appl. No.: 227,899

[22] Filed: Apr. 15, 1994

Related U.S. Application Data

[63] Continuation of Ser. No. 800,459, Nov. 26, 1991, abandoned.

[51] Int. Cl.$^5$ ............... D21C 1/00; D21C 3/00; D21C 3/20; D06M 11/00
[52] U.S. Cl. ................. 435/278; 435/277; 8/116.1; 162/72
[58] Field of Search ............ 435/278, 262, 277; 8/401, 116.1; 162/1, 9, 70, 72, 150

[56] References Cited

U.S. PATENT DOCUMENTS

| | | | |
|---|---|---|---|
| 4,649,113 | 3/1987 | Brimfield | 162/78 |
| 4,690,895 | 9/1987 | Farrell | 435/278 |
| 4,773,966 | 9/1988 | Huynh | 530/500 |
| 4,830,708 | 5/1989 | Paice et al. | 435/278 |
| 4,869,783 | 9/1989 | Prusas et al. | 162/18 |

FOREIGN PATENT DOCUMENTS

| | | | |
|---|---|---|---|
| 0430915 | 11/1990 | European Pat. Off. | |
| 0429422 | 5/1991 | European Pat. Off. | |
| 0433258 | 6/1991 | European Pat. Off. | |
| 3220389 | 9/1991 | Japan | D21C 3/00 |
| WO9102791 | 3/1991 | WIPO | D12N 9/24 |
| WO9102839 | 3/1991 | WIPO | D21C 9/10 |
| WO9102840 | 3/1991 | WIPO | D21C 9/10 |
| WO9105908 | 5/1991 | WIPO | D21C 9/10 |

OTHER PUBLICATIONS

Imai, T. "Plant Refining Method," Translation of Japanese Patent Document 03220389A2, (Sep. 27, 1991) pp. 1–10.

Morrison, I. "Influence of Chemical and Biological Pretreatments on the Degradation of Lignocellulosic Material by Biological Systems," *J. Sci. Food Agric.*, vol. 42 (1988), pp. 295–304.

Hoebler et al. "Study of Enzymatic Preparation of Cell Wall Residue," *Sciences Des Ailments*, vol. 10, (1990), pp. 255–263.

Database WPI, Section Ch, Week 9145, Derwent Publications, London Class D16, AN 91-329357 & JP-A-3 220 389, 27 Sep. 1991, Abstract.

Database WPI, Section Ch, Week 9208, Derwent Publications, London Class D16, AN 92-059463 & JP-A-4 002 895, Jan. 7, 1992, Abstract.

Dosoretz et al., "Effect of Environmental Conditions on Extra-cellular Protease Activity in Lignolytic Cultures of Phanerochaete Chrysosporium.", Feb. 1990, pp. 395–400. *Applied and Environmental Microbiology*.

CA108(21): 185366p Morrison, T. 1988.
CA116(2)8120y Imai, Y. 1991.
CA113(19)170595s Hoebler, et al 1990.

Bumpus et al "Oxidation of Persistent Environmental Pollutants by a White Rot Fungus" Science vol. 228 pp. 1434–1436 1985.

*Primary Examiner*—Michael G. Wityshyn
*Assistant Examiner*—Timothy J. Reardon
*Attorney, Agent, or Firm*—Thompson, Hine & Flory

[57] ABSTRACT

A method for the delignification of wood pulps by use of protease enzymes. Useful proteases include bromelain, pepsin and papain. The proteases are used to delignify the wood by degrading the wood protein, extensin.

11 Claims, No Drawings

PROTEASE CATALYZED TREATMENTS OF LIGNOCELLULOSE MATERIALS

This is a continuation of co-pending application Ser. No. 07/800,459, filed Nov. 26, 1991, now abandoned.

BACKGROUND

The present invention relates to an enzymatic treatment for wood chips or wood pulps which enhances fibrillation and facilitates delignification and bleaching.

Previous enzymatic and biopulping processes do not take into account the presence of extensin in cell walls. Extensin is a highly crosslinked protein, rich in proline and hydroxyproline which is not affected by xylanases and peroxidases such as ligninases. It is hypothesized that lignin is bound to extensin and functions as a supporting skeleton for cells. Extensin or lignin is most likely immobilized in cell walls during formation of the secondary wall.

Partial degradation of extensin would, therefore, appear to be important in making the lignin more accessible for extraction in chemical pulping and bleaching or to reduce energy consumption and damage to cellulose fibers during mechanical pulping.

SUMMARY OF THE INVENTION

In accordance with the present invention wood chips or wood pulps are treated at any stage of the papermaking process but preferably prior to delignification or bleaching with a protease enzyme to enhance fibrillation and/or the efficiency of delignification or bleaching. Tests by the inventors have shown that the proteases, pepsin and papain, promote the removal of lignin from wood, possibly through cleavage of the cell wall protein matrix. Tests have also shown that wood pulps treated with proteases in accordance with the invention exhibit a higher degree of fibrillation than pulps not treated with proteases. Tests have shown that protease treatment produces a flatter fiber which improves paper smoothness derived from these fibers. The protease treatment may be combined sequentially or by admixture with treatment with a xylanase or ligninase.

The theory which underlies the invention (as to which the applicants do not desire to be bound) is that cellulose polymer occurs in plants in an interwoven matrix of pectins, xylans (hemicellulose), lignin and protein. The structural role of the proteins has been explained using a "warp-weft" model which predicts a crosslinked protein network of extensins, hydroxyproline-rich proteins (HPRPs) and glycine-rich proteins (GRP's), which may be bound to lignin and cellulose. By hydrolyzing any of these protein systems, lignin removal is enhanced. It is also theorized that extensin may bind the microfibrils making up the fiber which may explain why enhanced fibrillation is observed with the protease treatment.

Depending on the nature of the wood chips or pulp, the wood chips or pulp may be treated directly with a solution of the protease enzyme. In other cases it may be desirable to pretreat the chips or pulp with an alkaline solution or a cellulase enzyme solution to remove materials which may coat the fibers. This enhances the access which the protease enzyme will have to the extensin in the fibers.

One manifestation of the invention is a method which comprises retaining wood chips in a solution of a protease enzyme for a period of time and under conditions sufficient to enhance delignification, bleaching or fibrillation of a pulp prepared from the wood chips.

Another manifestation of the invention is a method which comprises incubating cellulosic pulp in a solution of a protease enzyme for a period of time and under conditions which enhance delignification, bleaching or fibrillation of the pulp.

DETAILED DESCRIPTION OF THE INVENTION

While the enzymes used in the claimed methods are generally referred to as proteases, those skilled in the art will recognize that not all proteases will be equally effective against all substrates under all conditions. Any protease which is capable of hydrolyzing extensins, HPRP's and GRP's should be effective in the invention. As demonstrated in Examples 1 and 2 at the time of filing good results in terms of enhanced lignin removal have been achieved with pepsin (CAS No. 9001-75-6) and papain (CAS No. 9001-73-4). However, bromelain (CAS No. 37189-34-7) and fungal protease have not been found to be as effective in lignin removal. Particularly preferred proteases include natural or synthetic proteases which are active under less acidic or more basic conditions because acidic conditions tend to degrade pulp. For example, papain is active at a pH of 6.2 and is preferred to pepsin which requires a pH of 2.0. Preferred proteases exhibit their maximum activity at a pH greater than 4.0 and more preferably greater than 5.0. Even more preferred are proteases active under alkaline pH conditions.

Representative examples of proteases useful herein include subtilisins (CAS No. 9014-01-1), thermolysins (CAS No. 9073-78-3), bacterial proteases, such as Esperase (CAS No. 9073-77-2) and Alcace (CAS No. 9001-12-1), proteases exhibiting collagenase activity, proteases which hydrolyze gelatin, animal hoofs, horns, hides, ligaments, tendons or cartilage or hydrolyze other substrates which have a glycine and hydroxyproline content similar to that of plant cell wall proteins, proteases from sheep foot rot organisms, proteases from fungi that colonize wood such as blue stain fungi, white rot fungi and brown rot fungi.

Suitable pulps for the practice of invention include hardwood, softwood and other lignocellulosic pulps. By way of example, mechanical, themomechanical, chemimechanical, sulfite, kraft, soda and modified sulfite pulps may be used.

The protease treatment can be carried out in any vessel of the desired size with provision for mixing and controlling the temperature of the contents. Order of addition of reactants is not critical. The basic reaction mixture comprises pulp or wood chips in water at a pH appropriate for the enzyme or enzyme mixture used. In the case of a lignocellulosic pulp, the reaction mixture may range from about 1 to 16% in consistency. The protease is present in a ratio of about 1 to 1,000,000 units per gram dry pulp. One unit of protease will hydrolyze casein to produce color equivalent to 1 $\mu$mol of tyrosine per min. at 37° C. (color by Folin-Cicalteu Reagent). The reaction mixture is incubated at 20° to 80° C. for about 0.1 to 6 hours. Those skilled in the art will be able to readily optimize reaction conditions for the particular enzyme system without undue experimentation.

In accordance with one aspect of the invention, a xylanase, ligninase, pectin esterase, pectin lyase, or manganese peroxidase may also be used simultaneously or as a pretreatment or post treatment. Generally, these enzymes appear to make the extensin more accessible. For reaction of the xylanase reference can be made to International Application WO91/05908. For reaction of ligninase see European Patent Application 90810681.8.

Wood chips may be advantageously treated in accordance with the present invention by soaking them in a solution of the enzyme. However, the chips are preferably destructured by passage through a screw press as described in U.S. Pat. No. 4,869,783 to Prusas. By destructuring and compressing the chips and allowing the chips to expand in a solution of the enzyme, effective impregnation and infiltration of the chips is achieved.

Treatment of pulp in accordance with the invention may be coupled with any delignification or bleaching process to enhance the efficacy of those processes. Among other processes that may be coupled with that of the invention in making paper or board are oxygen delignification, hydrogen peroxide extraction and bleaching, chlorine dioxide bleaching, chlorine and chlorine dioxide bleaching, etc. The particular sequence of treatment is open. Any sequence including at least one stage in which chips or pulps are incubated with a protease are useful herein. The protease treatment may be positioned to advantage at any stage of the process sequence. However, for maximum efficacy in delignification, the protease treatment must precede the delignification and bleaching stage.

It is generally desirable to pretreat pulps to remove materials which may be deposited on the paper fibers and which may exhaust the protease. Many of these materials are alkaline soluble and, hence, it is desirable to wash the pulp with a sodium hydroxide solution (pH about 11 to 14) prior to the protease treatment. Where the pulp is manufactured under alkaline conditions, this may not be necessary. For example, alkaline pretreatment of kraft pulps is not necessary. Treatment with a surfactant or detergent may be used to enhance penetration of the protease into the fiber pores and to enhance washing of impurities and interfering substances. Pores may be opened by cellulase or pectinase pretreatments. Also treatment with chelators to remove metals may enhance penetration.

The alkaline pretreatment is generally carried out at 10° to 80° C. using about 5 to 200 parts alkali per 100 parts dry pulp. Another effective pretreatment is carried out at an alkaline pH and using about 50 to 5,000 cellulase units per 100 grams pulp or chips.

The invention is illustrated in more detail by the following non-limiting examples.

EXAMPLE 1

Cellulase Pretreatment

Refiner mechanical pulp (RMP) (750 g, 14% consistency) was mixed with 5 liters 0.1M sodium acetate, pH 5 and 20 g cellulase from *Penicillium funiculm* (134,000 units, Sigma Chemical Co.) and stirred for 2 h at room temperature. The slurry was filtered, stirred with 1 liter 2M sodium hydroxide for 30 minutes, filtered, washed with the same sodium hydroxide solution, filtered, washed with water three times and divided into 10 equal parts.

EXAMPLE 2

Protease Treatment

Cellulase treated and alkaline washed pulp (40 g) was equilibrated in 500 ml of the buffers shown in Table 1. The pH of the solutions were adjusted to the indicated level after addition of the pulp from Example 1. Proteases (2 g) were added to each slurry according to Table 1.

TABLE 1

Protease Treatment of Wood Pulp

| Protease | Buffer/pH (100 mM) | Enzyme Units[1] (Sigma Chemical Co.) |
|---|---|---|
| Control (Ex. 1) | Phosphate, 6.2 | 0 |
| Pepsin | Phosphate, 2.0 | 250,000 |
| Bromelain | Citrate, 4.5 | 3,750,000 |
| Fungal Protease | Phosphate, 2.8 | 1,200 |
| Papain | Phosphate, 6.2 | 5,600 |

[1]Units as defined by Sigma Chemical Co.

The protease treatment was conducted by stirring 1 hour at room temperature. The pulp was filtered, extracted with 100 ml 4% sodium borate in 2M sodium hydroxide, pH 12, followed by 100 ml 2M sodium hydroxide. Lignin removal was measured by determining the absorbance (OD) at 280 nm of each extract. The results are shown in Table 2.

TABLE 2

| Protease | Borate Extraction (OD 280 nm Units) | Hydroxide Extraction (OD 280 nm Units) | % Control |
|---|---|---|---|
| Control | 15.4 | .34 | 100 |
| Pepsin | 21.4 | .80 | 141 |
| Bromelain | 5.2 | 1.90 | 45 |
| Fungal Protease | 3.1 | .64 | 23 |
| Papain | 5.1 | 1.02 | 39 |

Results from Table 2 show that significantly more lignin is removed by treatment with pepsin than was removed from the untreated pulp. Some of the differences shown may be a function of extraction time and the pH of the control (6.2) incubation. Example 3 below examines effect of extraction time and pH on the comparison of lignin removal by protease treatment.

EXAMPLE 3

Example 3 was conducted as Example 2 using pepsin and papain only. However, the cellulase treated pulp was reduced to 30 g wet per test. Extraction time was lengthened to 85 minutes for the borate extraction and 100 minutes for the hydroxide extraction. The results are shown in Table 3.

TABLE 3

| Protease | Borate Extraction (OD 280 nm Units) | Hydroxide Extraction (OD 280 nm Units | % Control |
|---|---|---|---|
| Control, pH 2 | 1.36 | 1.87 | 100 |
| Pepsin, pH 2 | 6.28 | 2.15 | 261 |
| Papain, pH 6.2 | 2.80 | 2.18 | 154 |

Data shown indicated that for pepsin in particular the action of this enzyme enhances solubilization of lignin up to nearly 3-fold. These results show that proteases can promote removal of lignin from wood, possibly through cleavage of the cell wall protein matrix.

EXAMPLE 4

The purpose of this experiment is to demonstrate the effect of pretreatment on lignin removal. One sample of refined mechanical pulp was prepared without pretreatment. A second sample was prepared and washed in 2M NaOH. A third was treated with cellulase and washed with 2M NaOH. Each sample was treated with papain (phosphate buffer, pH=6.2) in the amounts shown in Table 3 followed sequentially by a water wash to remove protein and a borate extraction at pH=12 to remove lignin which separates the 280 nm contribution of the protein from that of the lignin and any other carbohydrates. The results are shown in Table 3 as percent of control (i.e., no protease enzyme).

TABLE 4

Effect of Pretreatments on OD 280 (Lignin) Extractibles from Refiner Mechanical Pulp. Percent Over Control (No Enzyme) - Borate Extraction OD 280

| Papain (grams) | No Pretreatment | Base Wash 2M NaOH | Pretreatments Cellulase Pretreatment + 2M NaOH Wash |
|---|---|---|---|
| 0.5 | 0.7 | 39 | 61 |
| 1.0 | 3.1 | 74 | 160 |
| 1.5 | 22 | 77 | 165 |
| 2.0 | 12 | 98 | 216 |

EXAMPLE 5

The effect of incubation time was determined by treating a mechanical pulp which had been treated with 2M NaOH pretreatment and incubated with 1 g papain under the time conditions shown in Table 5.

TABLE 5

Effect of Time of Incubation with Papain on Base Extractible from Refiner Mechanical Pulp.

| Time of Papain Incubation Minutes | Percent Increase in 280 nm Extractibles Over Zero Time Control |
|---|---|
| 15 | 111 |
| 30 | 134 |
| 45 | 160 |
| 60 | 130 |

The results in Table 5 show that the occurrence of increased extractibles is not an artifact of the treatment, but rather a time-dependent result of papain catalysis.

EXAMPLE 6

A kraft brownstock was treated with papain or bromelain without pretreatment under the condition shown in Table 6.

TABLE 6

| Amount of Protease Grams | Increase in Extractibles over Control (%) |
|---|---|
| Papain: | |
| 0.5 | 50 |
| 1.0 | 83 |
| 1.5 | 94 |
| 2.0 | 202 |
| Bromelain: | |
| 0.5 | 22 |
| 1.0 | 17 |
| 1.5 | 33 |
| 2.0 | 56 |

The results in table 6 show an increased effect of protease concentration on release of lignin from Kraft Brownstock pulp without further pretreatment. Both bromelain (protease from pineapple stems) and papain are effective, but the superior selectivity of papain is illustrated here.

Having described the invention in detail and by reference to preferred embodiments thereof, it will be apparent that modifications and variations are possible without departing from the scope of the invention defined in the appended claims.

What is claimed is:

1. A process for the delignification of lignocellulosic pulps which comprises treating a lignocellulosic pulp selected from the group consisting of hardwood or softwood mechanical, thermomechanical, chemimechanical, sulfite, kraft, and soda pulps with a solution of an isolated protease enzyme selected from the group consisting of bromelain, papain and pepsin, in an amount effective for delignification of said pulp at a temperature of about 20° to 80° C. under conditions and for a time sufficient for delignification of the pulp by said enzyme.

2. The process of claim 1 wherein said pulp is pretreated to enhance the infiltration of said pulp by said protease enzyme.

3. The process of claim 2 wherein the pretreatment includes treating said pulp with sodium hydroxide solution.

4. The process of claim 2 wherein the pretreatment includes treating said pulps with a cellulase enzyme solution.

5. The process of claim 1 wherein said process includes the additional step of treating said pulp with a xylanase enzyme to enhance said delignification.

6. The process of claim 1 wherein said protease is papain.

7. The process of claim 1 wherein said pulp is a mechanical pulp.

8. The process of claim 1 wherein said process further comprises further delignification or bleaching of said pulp after the treatment with said protease enzyme.

9. The process of claim 11 wherein the step of further delignification or bleaching is selected from the group consisting of oxygen delignification or bleaching, hydrogen peroxide extraction or bleaching, and chlorine or chlorine dioxide bleaching.

10. A process for enhancing delignification of lignocellulosic pulps which comprises treating wood chips with a solution of an exogenous isolated protease enzyme selected from the group consisting of bromelain, papain or pepsin, in an amount effective for delignification of said pulp at a temperature of about 20° to 80° C. for a time and under conditions sufficient for said enzyme to delignify said chips, and forming said chips into pulp.

11. The process of claim 8 wherein said chips are destructured prior to contacting said chips with said protease enzyme.

* * * * *

UNITED STATES PATENT AND TRADEMARK OFFICE
CERTIFICATE OF CORRECTION

PATENT NO. : 5,374,555
DATED : December 20, 1994
INVENTOR(S) : Alexander R. Pokora and Mark A. Johnson It is certified that error appears in the above-identified patent and that said Letters Patent is hereby corrected as shown below:

Claim 1, Col. 6, line 18, before the word "isolated" insert the word --exogenous--.

Claim 11, line 1, delete "8" and insert --10--.

Signed and Sealed this

Seventh Day of March, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,374,555
DATED         : December 20, 1994
INVENTOR(S)   : Alexander R. Pokora and Mark A. Johnson It is certified that error appears in the above-identified patent and that said Letters Patent is hereby corrected as shown below:

<u>Column 6,</u>
Line 43, delete "11" and insert -- 8 --.

Signed and Sealed this

Twenty-fifth Day of March, 2003

JAMES E. ROGAN
*Director of the United States Patent and Trademark Office*